United States Patent [19]

Bals et al.

[11] Patent Number: 5,331,845
[45] Date of Patent: Jul. 26, 1994

[54] PROBE AND METHOD FOR DETECTING ALCOHOL

[75] Inventors: Ion Bals, Cologny; John M. Hale, Meinier; Eugen Weber, Hinwil; Antoine Gagnebin, Geneva, all of Switzerland; Gérard R. Stehle, Machilly, France

[73] Assignee: Orbishpere Laboratories Neuchatel SA, Switzerland

[21] Appl. No.: 5,264

[22] Filed: Jan. 19, 1993

[51] Int. Cl.⁵ ............................. G01N 7/10
[52] U.S. Cl. ........................ 73/61.43; 73/19.1
[58] Field of Search ................ 73/61.43, 19.1

[56] References Cited

U.S. PATENT DOCUMENTS

| | | |
|---|---|---|
| 3,438,241 | 4/1969 | McKinley . |
| 3,673,853 | 7/1972 | Griswold et al. . |
| 3,731,523 | 5/1973 | Vissers et al. . |
| 3,866,460 | 2/1975 | Pearce . |
| 3,871,228 | 3/1975 | Weiss . |
| 4,201,550 | 5/1980 | Nosticzius et al. . |
| 4,316,382 | 2/1982 | Woodruff . |
| 4,365,505 | 12/1982 | Holzl . |
| 4,402,211 | 9/1983 | Sugawara et al. . |
| 4,461,165 | 7/1984 | Kesson . |
| 4,463,593 | 8/1984 | Parker . |
| 4,516,580 | 5/1985 | Polanyi . |
| 4,517,135 | 5/1985 | Szerenyi et al. . |
| 4,550,590 | 11/1985 | Kesson . |
| 4,563,249 | 1/1986 | Hale . |
| 5,121,627 | 6/1992 | D'Aoust . |
| 5,144,831 | 9/1992 | Hale . |

FOREIGN PATENT DOCUMENTS 258284 7/1988 Fed. Rep. of Germany ..... 73/61.43

*Primary Examiner*—Hezron E. Williams
*Assistant Examiner*—Joseph W. Roskos
*Attorney, Agent, or Firm*—Wigman, Cohen, Leitner & Myers

[57] ABSTRACT

A probe for measuring the concentration of an alcohol, such as ethanol, in a liquid, such as water. The probe according to the invention has a membrane that is permeable for vapors of the alcohol but substantially impermeable for the liquid; a measuring chamber having an open end closed against the liquid by the membrane is provided and has an inlet and an outlet; a pump or other pressure means serves to feed a purge gas, such as air, via the inlet into and out of the measuring chamber; a valve is provided near the inlet for controlled passage of the purge gas through the chamber; a suitably dimensioned detector including a pellistor or a gas-sensitive resistor is arranged in the measuring chamber for quantitative detection of the alcohol and for generating an electrical signal in proportion with the detection.

20 Claims, 3 Drawing Sheets

PROBE AND METHOD FOR DETECTING ALCOHOL

CROSS-REFERENCE TO RELATED APPLICATIONS

The present application concerns subject matter that is related to subject matter disclosed in copending U.S. patent application Ser. No. 07/614,133 filed Nov. 16, 1990, now issued as U.S. Pat. No. 5,144,831 in the names of John Martin HALE and Eugen WEBER as well as in copending U.S. patent application Ser. No. 07/840,943 filed in the names of John Martin HALE, Eugen WEBER and Gérard Roland STEHLE on Feb. 25, 1992 as a continuation-in-part application of the said first-mentioned patent application, now issued as U.S. Pat. No. 5,255,553.

BACKGROUND OF THE INVENTION

1. Field of the Invention

The present invention concerns a probe and a method for detecting alcohols such as typically ethanol or other alcohols capable of forming a gas or vapor phase. Detection of ethanol is of primary importance herein, it being understood that the term "detecting" refers to a quantitative rather than a merely qualitative measurement.

A field of particular interest for the present invention is the in-line determination of a concentration of ethanol in an "inert" liquid, i.e. any liquid that is not capable of forming an oxidizable vapor, such as typically water, e.g. in the form of the aqueous phase of a beverage.

2. Description of the Prior Art

In-line measurement of the concentration of ethanol in a liquid, e.g. an alcoholic beverage, is a problem hitherto solved typically by direct measurement of a combination of two physical properties, such as density, refractive index or sound velocity. Apart from the expense and inconvenience of the use of two independent sensors, such prior art methods suffer interference from variations of pressure, dissolved carbon dioxide, and carbohydrate concentrations.

OBJECTS AND SUMMARY OF THE INVENTION

Accordingly, it is a primary object of the present invention to provide for a single selective sensor and a method capable of rapidly and reproducibly measuring such concentrations in a continuous manner, with a quick response to concentration changes, and without a risk of contamination of the analyzed fluid.

This object and further advantages are achieved in a first embodiment of the invention by means of a probe for measuring a concentration of a normally volatile alcohol in a liquid comprising: (A) a membrane that is permeable to vapors of said alcohol but substantially impermeable to said liquid; (B) a measuring chamber having an open end closed against said liquid by said membrane and having an inlet and an outlet; (C) a pressure means for feeding a purge gas via said inlet into said measuring chamber and out of said chamber by means of said inlet and said outlet, and at least one valve for controlling passage of said purge gas through said measuring chamber; and (D) a detector arranged within said measuring chamber capable of an essentially quantitative detection of said alcohol and of generating an electrical signal in proportion with said detection.

DESCRIPTION OF PREFERRED EMBODIMENTS OF THE INVENTION

According to a first preferred embodiment said detector includes a reaction means capable of an essentially quantitative exothermal reaction with said alcohol; a first preferred type of such a detector includes a pellistor, i.e. a resistor-based device of the type explained in more detail below. Depending upon the type of detector used the probe contains a catalytic means capable of oxidizing the alcohol in the presence of oxygen.

A second preferred type of a detector for use in the invention is a gas-sensitive semiconductor also explained in more detail below.

A third preferred type of a detector for use in the invention is a piezoelectric quartz crystal provided with a coating capable of reversibly absorbing or adsorbing alcohol.

A fourth preferred type of detector for use in the invention is a photoacoustic detector, i.e. a measuring volume or chamber equipped with a pulsed or chopped infrared source and a microphone.

In a second embodiment of the invention there is provided a method of measuring a concentration of a normally volatile alcohol in a liquid comprising: (E) contacting said liquid with a membrane that is permeable to vapors of said alcohol but substantially impermeable to said liquid; (F) providing a measuring chamber having an open end closed against said liquid by said membrane and having an inlet port and an outlet port; (G) providing a detector within said measuring chamber capable of an essentially quantitative detection of said alcohol and of generating an electrical signal in relation with said quantitative detection; (H) providing an indicator capable of converting said signal into an indication of said concentration of said alcohol in said liquid; and (I) intermittently purging said measuring chamber with a controlled stream of a purge gas fed into said inlet port of said measuring chamber.

Generally, it is preferred that the purge gas contains a component capable of oxidizing alcohol in an exothermic reaction; frequently it is preferred that the purge gas includes carbon tetrachloride, preferably in the form of air saturated therewith.

It has been found that with a probe according to the invention, response times of less than 10 minutes, e.g. 5 minutes, can be obtained for a 90% response with a sensitivity in the order of 1 mbar (millibar; partial pressure of the vapor of the alcohol of interest) as will be explained in more detail below, and such response can be obtained in an essentially continuous manner and in in-line operation of the probe, e.g. while connected with a vessel or conduit containing the medium in which the alcohol or ethanol concentration is to be measured. In the context of using a probe for continuous in-line operation it is a particular advantage of a probe according to the invention that it can be operated in a perfectly sanitary fashion, i.e. without the risk of biocontamination, such as by microorganisms including bacteria and fungi.

The term "alcohol" as used herein is intended to encompass organic hydroxy compounds which are capable of generating an oxidizable or combustible vapor; preferred alcohols are those having a boiling point of below 120° C., preferably below 100° C. Ethanol is a preferred species but methanol, propanol and propenol (allyl alcohol) can be cited by way of further examples.

A "membrane" as used herein is a normally flexible film formed essentially of a synthetic homopolymer, copolymer graft polymer or a mixture of such synthetic organic polymers. The film must be permeable for vapors of the alcohol concerned but must be substantially impermeable for any liquids in which the alcohol might be contained when being measured. Films or "foils" of such polymers as polytetrafluoro ethylene, silicone rubber, and other polymers known to be suitable for use with membrane-enclosed sensors in the electroanalytical art can be used. Membrane thickness will depend upon permeability of the membrane material in question for the alcohol of interest as well as upon physical and chemical stability of the membrane material under operating conditions (typically in the temperature range between $-20°$ and $+100°$ C). Typical membrane thicknesses will be in the range of from 5 to 500 $\mu$m (micrometers) with a preferred range between 10 and 200 $\mu$m.

A "liquid" in the sense used herein is any substance that is liquid under normal conditions and does neither permeate through the membrane nor dissolve or otherwise attack the membrane and produces no vapors that would interfere with the intended measurement of the concentration of the alcohol of interest. Obviously, liquids capable of generating an oxidizable vapor would interfere.

The measuring chamber is a discrete element having an open end closed against said liquid by said membrane, as well as an inlet port and an outlet port; preferably, the free volume (i.e. the volume portion of the chamber that is accessible to alcohol vapor) of the measuring chamber is small, e.g not exceeding about 1000 $\mu$l (microliters). A typical preferred free volume range is between 50 and 500 $\mu$l.

The pressure means can be a pump for electric, pneumatic or hydraulic actuation, or a pressurized gas, e.g. air, or another gas mixture that includes, or substantially consists of, an oxidizing gaseous material supplied from a pressurized container, or an equivalent device capable of producing a gas flow of at least about 5 times the volume of the measuring chamber per minute. Conduits for connecting the pressure means with the measuring chamber can be formed within the probe housing and suitable connecting lines can be formed of metal or plastic; at least one valve for rapidly and automatically closing and opening the access to the measuring chamber, e.g. a valve actuated by a solenoid, is provided and is preferably arranged in the inlet conduit; suitable pressure means including pumps as well as valves for use in or with a probe according to the invention are available from commercial sources.

The measuring chamber includes a detector capable of an essentially quantitative detection of the alcohol, and capable of generating an electrical signal in proportion with the detection; obviously, the detector must be small enough to fit into the probe.

A first preferred example of such a detector is a so-called pellistor, i.e. a solid state sensor of the type known also as catalytic calorimeter or microcalorimeter. Generally speaking, it is a device that is capable of converting heat exchanged in a chemical reaction into an electrical signal. Such devices are known per se and are described, for example, by Nuscheler, E., in Proc. 2nd Int. Meeting on Chemical Sensors, Bordeaux 1986, 1-33, pages 235-238, incorporated herein by way of reference. Suitable pellistors are available e.g. from Microsens S. A. of Neuchatel, Switzerland, Siemens AG, Germany, and Cerchar Sarl, France. Generally, for use in the present invention, the pellistor includes a catalyst capable of oxidizing the alcohol of interest. Typically, the pellistor is composed of two heated resistors operating typically at a temperature in the order of 300° C. One resistor, coated with an inert layer, acts as a reference resistor.

The other resistor is coated with a catalytic material with a good efficiency for oxidation of alcohol or ethanol, respectively. Typical examples include platinum, palladium, copper oxide, vanadium oxide, rhodium, titanium oxide, ruthenium, molybdenum, magnesia and silver.

The oxidation of alcohols in the presence of air (oxygen) is exothermic and the heat generated is a direct function of the amount of alcohol that has been oxidized. The resulting temperature increase of the sensitive resistor induces a change of the resistance value which can be detected by means of a Wheatstone bridge. Typical voltages applied to the pellistor are in the order of about 5 V; typical currents are in the order of about 25 mA.

Another preferred example of a detector suitable for the invention is a gas-sensitive resistor of the type also known as Tagushi sensor, Figaro sensor, metal oxide sensor and tin oxide (actually tin dioxide, $SnO_2$) sensor. Generally speaking, such devices comprise a metal oxide surface that will change its conductivity in response to the adsorption of a gas on the metal oxide surface. Again, such devices are known and have been described, e.g. by Bergveld, P., in the publication cited above, pages 49-58, incorporated herein by way of reference. Suitable devices are obtainable from commercial sources, e.g. from the Figaro Company, Japan, or the Fraunhofer Institut für physikalische Messtechnik (Germany) or Microsens SA (Switzerland).

Another detector or detection principle is based on a piezoelectric quartz crystal. This type of detector is known per se and has been described in detail in the book by Lu and Czandera with the title "Applications of piezo-electric quartz crystal microbalances" (Elsevier 1984) incorporated herein by way of reference. Various coatings on the quartz crystal will make it selectively sensitive to alcohol. Typical examples of such coatings include organic polymers as well as inorganic materials (e.g. ceramics or "molecular sieves" such as zeolites) deposited by spin coating, plasma deposition, sputtering, physical or mechanical deposition, chemical vapor deposition, or another method known to be suitable for deposition of films with a thickness in the typical range of from about 10 nm (nanometers) to 100 $\mu$m (micrometers). Quartz microbalances are available commercially from various sources including Leybold-Inficon (USA), Balzers AG (Liechtenstein), Edwards Ltd (United Kingdom).

An accumulation of alcohol in the measuring volume, space or chamber during the measurement cycle according to the invention will cause an increase of the mass of the surface coating and induce a corresponding shift in the resonance frequency of the quartz crystal. When the alcohol is removed from the measuring volume, the mass of the surface coating will decrease and induce a reverse shift in the resonance frequency of the quartz crystal.

A further means of detecting trace amounts of alcohol in the measuring volume or chamber during the measurement cycle according to the invention is photoacoustic (or optoacoustic) spectroscopy. Devices suitable for such photoacoustic spectroscopy generally comprise three essential components, vz. (i) a measuring space or chamber, (ii) an excitation source, such as typically a laser or lamp, and (iii) a microphone. When absorbed by a specific gas, the excitation energy is converted to heat so as to cause an increase of pressure. By chopping the excitation beam, successive pressure surges or pulses will generate a sound corresponding to the chopping frequency. Such sound will be detected by the microphone and converted into an electrical signal in synchronicity with the excitation pulses.

This technique is known per se and is discussed in detail in "Optoacoustic spectroscopy and detection" by Yoh-Han-Pao (Academic Press 1977), also incorporated herein by way of reference. Suitable excitations sources can be obtained commercially, e.g. from Zeiss (Germany) or PMS Electro-optics (USA). Suitable alternative sources for infrared radiation are manufactured by Oriel (USA) and Osram (Germany). Suitable microphones can be obtained from various sources, e.g. AKG-Telefunken (Germany), Panasonic (Japan) or Brüel and Kjaer (Denmark).

For carrying out the method according to the invention, the liquid as defined above (also termed "ambient" liquid) is contacted with the membrane such that vapor of the alcohol of interest but not the ambient liquid will permeate the membrane and enter into the measuring chamber; the electrical signal that is generated by the detector is fed into an indicator, preferably after suitable amplification. Generally, the primary signal can be used for generating the desired final output signal in the manner disclosed in the above-mentioned U.S. patent applications, notably in Ser. No. 07/840,943.

The measuring chamber is purged intermittently, e.g. with a cycling period of between 10 and 300 seconds and with a controlled (in terms of flow rate, temperature and pressure) stream of a purge gas fed into the inlet port of the measuring chamber. Air or mixtures of air with specific additives for accelerated reset, such as carbon tetrachloride or hydrogen, are mentioned by way of example.

BRIEF DISCUSSION OF THE DRAWINGS

The invention will now be discussed in more detail with reference to the enclosed drawings illustrating the invention without limitation and in which.

Figure 1:
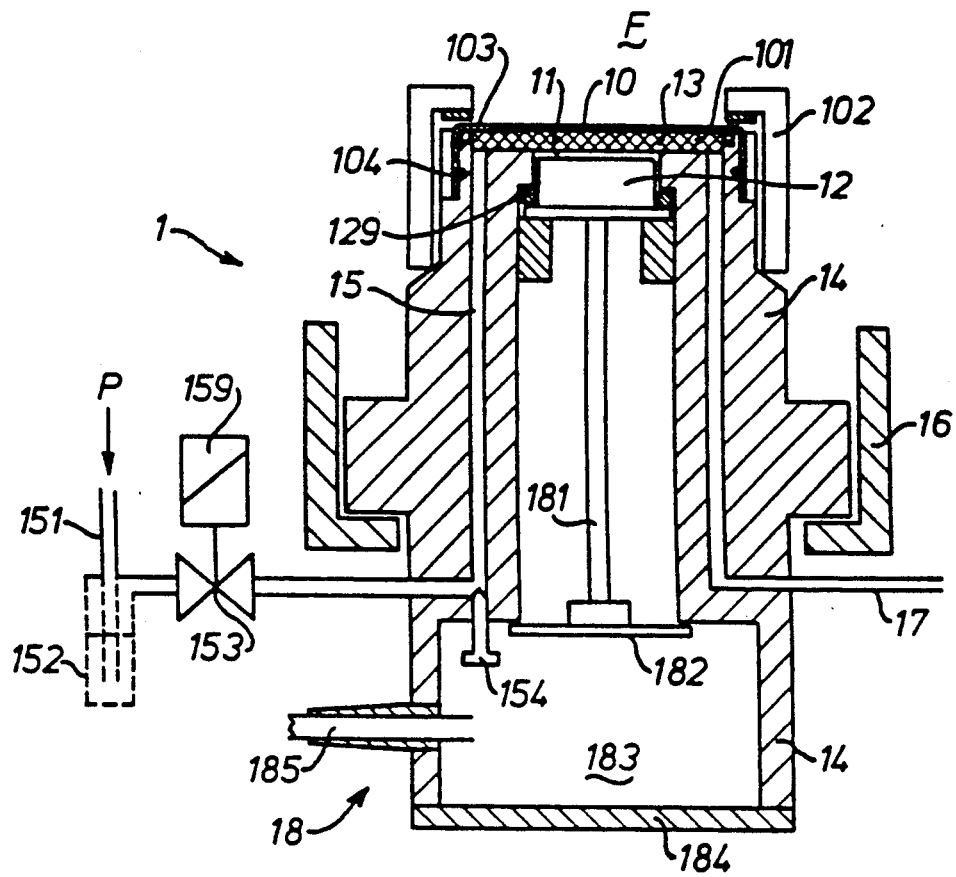
FIG. 1 is a diagrammatic view of a probe according to the invention.

Probe 1 shown schematically in FIG. 1 includes a membrane 10 permeable for vapors of alcohols, e.g ethanol, and consisting typically of a thin film having a thickness in the range of from about 10 to about 50 $\mu$m, e.g. 17 $\mu$m, made of a polymer such as PTFE. Membrane 10 is held by a support member 13, typically a porous solid layer such as a mesh 101, made for example of metal and held in position within the measuring chamber 11 by a cap 102. Sealing of membrane 10 is effected by means of O-rings 103, 104.

The interior free volume of chamber 11 is as small as feasible and is formed essentially by the openings within support 13, on the one hand, and any gaps between the detector 12 and both the support 13 as well as the probe housing 14, on the other. A sealing means, e.g. O-Ring 129, is used to seal detector 12 within chamber 11 such that the open end thereof (defined essentially by the membrane-contacting surface portion of support 13 in FIG. 1) is closed by membrane 10.

Probe housing 14 is held in place, in a manner known per se, by a mounting collar 16 connected (in a manner not shown) with a measuring site or space containing the external fluid F which, in turn, contains, or is suspected to contain, the alcohol of interest.

Detector 12 can be a commercially available device, such as a gas-sensitive resistor or a pellistors, or a specially designed detector, based either on a modified quartz crystal microbalance or on an optoacoustic spectrometer as described herein above.

An inlet conduit 15 opens into that portion of chamber 11 which is essentially defined by voids in support 13. Ambient air or another suitable purge gas is introduced via inlet 151 by a pressure means P which might either be a pressure source (e.g. container containing a gas under pressure; not shown) or a pump (not shown) connected with inlet conduit 15 or with outlet conduit 17. A valve 153 for closing and opening conduit 151 is operated by an automatic actuator, e.g. a solenoid 159.

A needle valve 154 serves to maintain a controlled maximum rate of flow of the purge gas through inlet conduit 15 into chamber 11 and through exit conduit 17. Valve 154 can be actuated manually or by an electric or equivalent actuator provided within the signal-processing chamber 183 to be explained in more detail below.

The purge gas (which should contain an oxidizing constituent such as oxygen) or air that enters into conduit portion 151 may be passed through a trap or bubbler 152 filled with a liquid capable of producing a purging additive, such as carbon tetrachloride or another halohydrocarbon. It has been found according to the invention that a significant acceleration of purging or "resetting" can be achieved in this manner. For example, when operating a probe according to the invention with a gas-sensitive resistor of the preferred $SnO_2$ type as the detector for measuring ethanol, a complete reset to "zero-conditions" with air as the purge gas may take 10 to 30 minutes while a reset time of 10 to 30 seconds can be achieved when the purge gas is air which has been saturated with carbon tetrachloride or the like contained as a liquid phase in bubbler 152.

Outlet conduit 17 can be connected (not shown) with a filter or other device, e.g. a cold trap, to recover the additive from the purge gas and to prevent environmental problems.

Valve 153 with its solenoid drive 159 is used to alternate the probe between "open" and "closed" cycling periods where the free interior volume of measuring chamber 11 is flushed or purged, or is maintained for undisturbed interaction between the detector and the alcohol vapor that has permeated from the external fluid F through membrane 10 into the measuring chamber 11 formed within support 13 and any communicating gaps between detector 12 and immediately adjacent structures.

An electronic processor 18 is supplied with the primary probe signal produced by detector 12 in response to a given concentration of an alcohol contained in ambient fluid F; the primary signal is passed via an electric connector 181 through a closure plate 182 of the signal processing chamber 183; plate 182 may carry a printed circuit (not shown in FIG. 1) for processing and amplifying the primary signal in a manner known per se and passing the secondary signal via an output connector, e.g. cable 185, to a computing device (not shown) for analysis of the secondary signal and, finally, to an output indicator (not shown) which may be a digital or analogue display, a recorder or other known signal output device.

Figure 2:
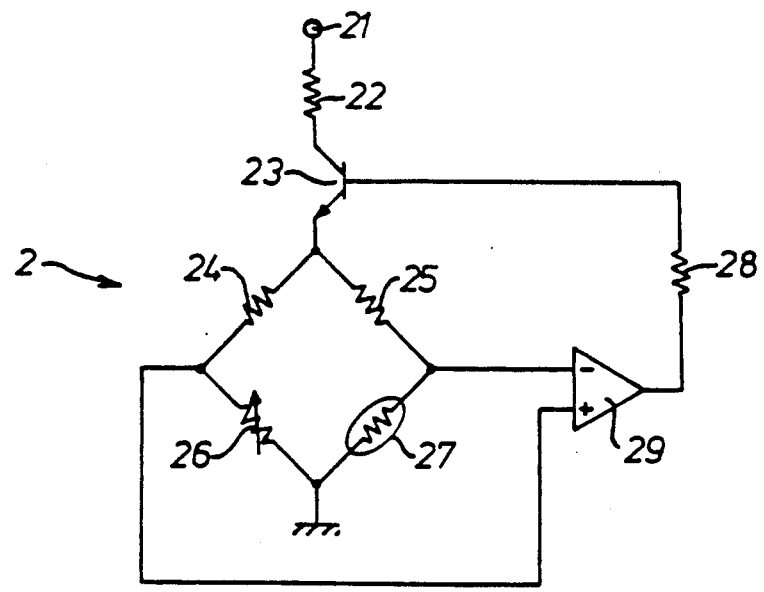
FIG. 2 is a diagrammatic view of the heating element which forms part of the electronic circuit of the probe illustrated in FIG. 1 when using a gas-sensitive detector device.

FIG. 2 illustrates an example of a circuit 2 for maintaining the heating element of a preferred gas-sensitive resistor of the SnO$_2$ type at a constant temperature in the manner of a Wheatstone bridge configuration. A DC voltage of for example +15 Volts is applied at 21. The current flowing in each branch of the Wheatstone bridge of FIG. 2 generates a voltage drop at the opposite corners of the bridge. As heater element 27 gets warmer, its resistance increases and so does the voltage on the inverting input of comparator 29. As a consequence the driving current of transistor 23 will be reduced thus decreasing the total current flowing in the bridge of FIG. 2. When the heating element 27 cools down, the voltage on the inverting input of comparator 29 becomes smaller than the voltage on the non-inverting input.

Consequently, the comparator will generate a larger input in the base of transistor 23 thus allowing more current to be fed into the bridge. A suitable temperature of heating element 27 (e.g. in the order of 300° C.) can be selected by adjusting variable resistor 26.

Figure 3:
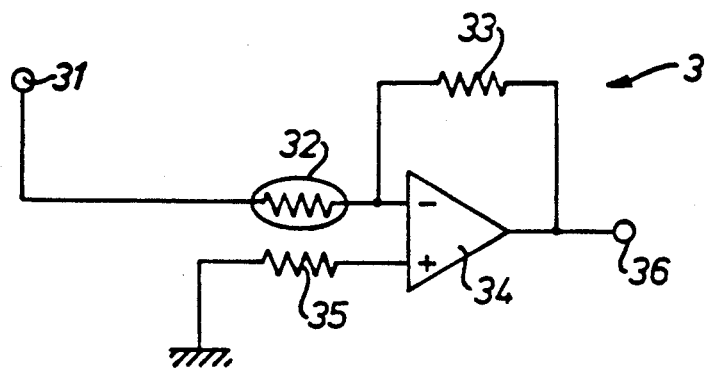
FIG. 3 is a diagrammatic representation of the circuit including a sensitive $SnO_2$ layer for use as the detector in a probe as shown in FIG. 1 with the circuit shown in FIG. 2.

FIG. 3 illustrates an example of a circuit 3 including the SnO$_2$ sensitive layer of a probe detector according to the invention. It operates in the manner of a conventional current-to-voltage converter. With a fixed voltage (for example 5 Volts) applied at 31, a variable current will flow in the gas-sensitive resistor 32, depending on its gaseous environment. By means of circuit 3, a voltage will be generated at 36 equal to this current and multiplied by the value of resistor 33. For example, if resistor 33 is, for example, 1 MOhm, a current of 1 $\mu$A flowing through gas-sensitive resistor 32 will generate an output of 1 V on amplifier 34. Circuits of this general type are well known in the art.

Figure 4:
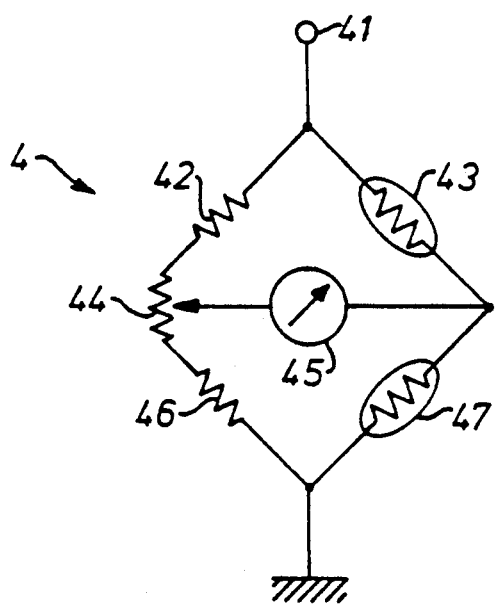
FIG. 4 is a diagrammatic view of an electronic circuit for use in a probe according to FIG. 1 when operating with a pellistor.

FIG. 4 illustrates the electronic circuit 4 for a pellistor suitable as the detector of a probe according to the invention. Circuit 4 is supplied at 41 with DC current of +5 V and fed into a Wheatstone-type circuit including resistor 42 (1 K$\Omega$), reference heater 43, a device 45 for generating output signal V$_{out}$, a variable resistor 44 (1 K$\Omega$), resistor 46 (1 K$\Omega$) and a catalytic heater 47. Circuits of this general type are known in the art and need not be elaborated further herein.

Figure 5:
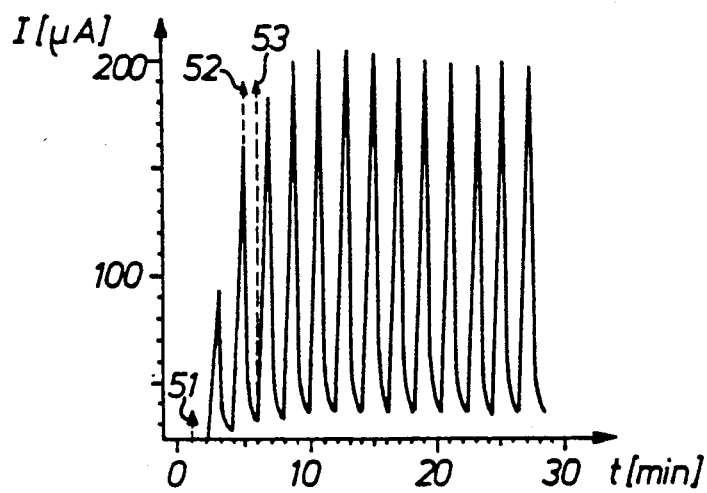
FIG. 5 is a recording of a typical probe signal obtained with a probe in accordance with FIG. 1 when operating with a gas-sensitive detector for measuring ethanol with alternating measuring and purging cycles.

FIG. 5 illustrates a recording of a typical raw output signal of a probe operated according to the invention essentially as indicated above using a gas-sensitive resistor of the SnO$_2$ type as detector 12. Current output I in nA (Nanoamperes) is indicated on the ordinate while time t in minutes is indicated on the abscissa. Point 51 indicates the moment of ethanol injection; peak 52 indicates the start while trough 53 corresponds with the end of a purging cycle (valve 153 in open position); conversely, each trough 53 indicates the start of a measuring cycle (valve 153 in closed position) while each peak 52 indicates the end of a measuring cycle. An essentially stable value of successive peak points 52 is reached after about 10 minutes and four alternating purging and measuring cycles.

Figure 6:
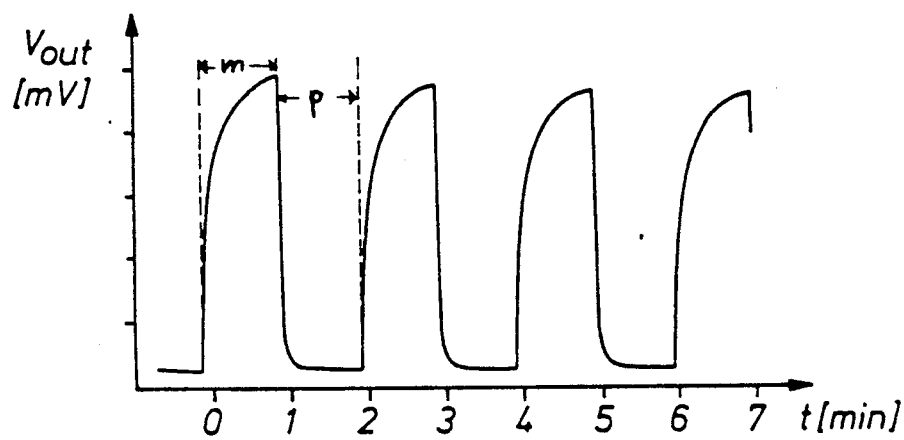
FIG. 6 is a recording of a typical probe signal obtained from a probe as shown in FIG. 1 when operating with a pellistor as illustrated in FIG. 4 for measuring ethanol.

FIG. 6 shows a recording of a typical raw output signal from a probe according to the invention operated with a pellistor as detector 12; the V$_{out}$ signal in mV (millivolts) is indicated on the ordinate, the time t in minutes on the abscissa. Pure ethanol at 25° C. was used as the external fluid; membrane 10 was a silicone membrane of 125 $\mu$m Double arrow "m" indicates the measuring phase, double arrow "p" the purging phase.

Figure 7:
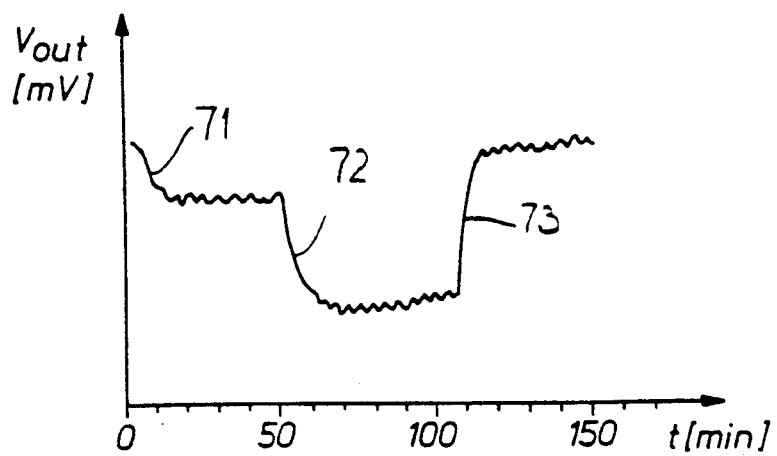
FIG. 7 is a recording of an output signal when measuring step changes of the ethanol concentration with a probe as illustrated in FIG. 1 when using either a gas-sensitive $SnO_2$ device or a pellistor as the detector.

FIG. 7 is the trace of an analyzer output obtained with a chart recorder. Output signal V$_{out}$ in mV (inversely, lower values up) is given on the ordinate, the time in minutes on the abscissa.

Standard ethanol levels were obtained by bubbling air in ethanol at fixed temperatures; a temperature of $-20°$ C. corresponds to a 4 mbar ethanol pressure while a temperature of $-10°$ C. corresponds to 8,1 mbar of ethanol (partial pressures).

A first signal step 71 was recorded when changing from pure air to an ethanol-air mixture saturated at $-20°$ C. as the external fluid while a second signal step 72 was recorded when changing to an ethanol-air mixture saturated at $-10°$ C. Step 73 was recorded when changing back to passing pure air as the external fluid. Each step change was essentially complete after about 5 minutes.

The following examples are given by way of illustration, not limitation.

EXAMPLE 1

A probe essentially as shown in FIG. 1, was inserted into the flow chamber through which the ethanol-containing fluid was passed. Solenoid valve I 53 was opened to let a mixture of air and CCl$_4$ flush the porous support 13, the chamber 11 and the tin dioxide sensor therein. After 1 minute the signal current became essentially stable at typically about 200 nA. Then, valve 153 was closed for 1 minute and the value of the current flowing through the sensitive layer of the detector was recorded. In the absence of ethanol (passage of pure water) the value reached at the end of the purge cycle remained constant during 1 minute.

With pure ethanol present at 25° C., a steady increase of the current of typically 20 nA per minute was observed with the circuit of FIG. 3. Different alcohol/water mixtures yield different slopes, linearly proportional to the alcohol partial pressure of the mixtures concerned. Standard formulae can be used for calculation of the volume fraction of alcohol from the partial pressure measured.

Each purge (open valve condition) cycle after a measuring (closed valve condition) cycle resets the signal current to its previous value. As a result, a continuous "saw-tooth" curve is obtained (FIG. 5). Computing the slopes and compensating for temperature and admixture effects yields an updated alcohol or ethanol indication every 2 minutes.

EXAMPLE 2

This example was carried out using a probe fitted with a pellistor as the detector. Generally, when operating according to the invention, the resistor bridge of FIG. 4 is equilibrated at around Zero Volt during each purge cycle. Once the purge is stopped, the alcohol permeating through the membrane accumulates in the free space of the measuring chamber 11. At the same time, catalytic heater 47 oxidizes the alcohol present in the probe. The form of the resulting signal is as shown in FIG. 6. It rises sharply and the initial slope is proportional to the rate of entrance of the alcohol into chamber 11, typically in the order 5 to 50 mV/min for 5% ethanol in water at 25° C., depending upon the permeability of membrane 10. Then the curve flattens out and reaches a steady plateau. At this stage, the rate of alcohol permeation through membrane 10 equates its rate of oxidation on the catalytic heater 47.

Accordingly, a probe according to the invention can be operated in two different modes:

(i) Operation in a cyclic mode; in this mode, the initial slope of the signal is measured and, after suitable correction for temperature and any other contributing parameters, the vapor pressure of the alcohol of interest in the external fluid F can be determined.

(ii) Operation in continuous mode; in this mode, the steady state signal is used as a measure of the alcohol permeation rate through membrane 10. A continuous supply of oxygen into the measuring chamber and the detector therein is required for oxidative removal of the permeated alcohol. This mode of operation is similar to that of an amperometric or Clark sensor as disclosed, e.g. in U.S. Pat. No. 4,096,047 and the art discussed therein. In this mode of operation, a slow drift or shift in the balance of the Wheatstone bridge (FIG. 2 and FIG. 4) may introduce a corresponding drift or shift in the alcohol reading and may require compensation.

Various modifications of probe structure and probe operation will be apparent to those experienced in the art. For example, the structure of the probe may be modified to increase or decrease the free volume of the measuring chamber, to modify the circuitry as well as the operating conditions. Any such modifications are within the scope of the present invention as defined in the subsequent claims. Probe and method according to the invention are of use for quantitatively measuring and continuously monitoring other organic substances than alcohols provided that such substance is capable to produce an oxidizable vapor under ambient conditions or at elevated temperatures. In other words, vapors of suitable substances must be capable of combustion. Also, inorganic substances that produce, or exist as, an oxidizable gas or vapor can be measured quantitatively, and monitored continuously according to the invention include such substances as hydrogen, carbon monoxide and the like. While various devices for continuously monitoring such substances are commercially available, it is believed to be an added advantage of the invention that it is of use for widely varying analytic applications.

Accordingly, what we claim is:

1. A probe for measuring a concentration of a normally volatile alcohol in a liquid comprising:
   (A) a membrane that is permeable to vapors of said alcohol but substantially impermeable to said liquid;
   (B) a measuring chamber having an open end closed against said liquid by said membrane and having an inlet and an outlet;
   (C) a pressure means for feeding a purge gas via said inlet into said measuring chamber and out of said chamber by means of said outlet, and at least one valve for controlling passage of said purge gas through said measuring chamber; and
   (D) a detector arranged within said measuring chamber capable of an essentially quantitative detection of said alcohol and of generating an electrical signal in proportion with said detection.

2. The probe of claim 1 wherein said detector includes a pellistor.

3. The probe of claim 1 wherein said detector includes a gas-sensitive resistor.

4. The probe of claim 1 wherein said detector includes a quartz crystal microbalance.

5. The probe of claim 1 wherein said detector includes an optoacoustic spectrometer.

6. A probe as in claim 1, wherein said membrane has a free surface for direct exposure to the liquid.

7. A method of measuring a concentration of a normally volatile alcohol in a liquid comprising:
   (E) contacting said liquid with a membrane that is permeable to vapors of said alcohol but substantially impermeable to said liquid;
   (F) providing a measuring chamber having an open end closed against said liquid by said membrane and having an inlet port and an outlet port;
   (G) providing a detector within said measuring chamber capable of an essentially quantitative detection of said alcohol and of generating an electrical signal in relation with said quantitative detection;
   (H) providing an indicator capable of converting said signal into an indication of said concentration of said alcohol in said liquid; and
   (I) intermittently purging said measuring chamber with a controlled stream of a purge gas fed into said inlet port of said measuring chamber.

8. The method of claim 7 wherein said detector includes a pellistor.

9. The method of claim 7 wherein said detector includes a gas-sensitive resistor.

10. The method of claim 9 wherein said probe contains a catalytic means capable of oxidizing said alcohol in the presence of oxygen.

11. The method of claim 7 wherein said detector includes a quartz crystal microbalance.

12. The method of claim 7 wherein said detector includes an optoacoustic spectrometer.

13. The method of claim 7 wherein said probe contains a means capable of selectively adsorbing said alcohol.

14. The method of claim 7 wherein said purge gas contains a component capable of oxidizing alcohol in an exothermic reaction.

15. The method of claim 7 wherein said purge gas includes carbon tetrachloride in the form of air saturated therewith.

16. A method as in claim 7, wherein said membrane has a free surface for direct exposure to the liquid.

17. A probe for in-line measurement of a concentration of a normally volatile alcohol in a process stream of liquid comprising:
   (A) a membrane that is permeable to vapors of said alcohol but substantially impermeable to said liquid, said membrane disposed in the vicinity of said liquid process stream;

(B) a measuring chamber having an open end closed against said liquid by said membrane and having an inlet and an outlet;

(C) a pressure means for feeding a purge gas via said inlet into said measuring chamber and out of said chamber by means of said outlet, and at least one valve for intermittently controlling passage of said purge gas through said measuring chamber, said valve adapted for cyclical purging of said measuring chamber; and (D) a detector arranged within said measuring chamber capable of an essentially quantitative detection of said alcohol and of generating an electrical signal in proportion with said detection.

18. A method of in-line measurement of a concentration of a normally volatile alcohol in a process stream of liquid comprising:

(E) contacting said liquid with a membrane that is permeable to vapors of said alcohol but substantially impermeable to said liquid, said membrane disposed in the vicinity of said liquid process stream;

(F) providing a measuring chamber having an open end closed against said liquid by said membrane and having an inlet port and an outlet port;

(G) providing a detector within said measuring chamber capable of an essentially quantitative detection of said alcohol and of generating an electrical signal in relation with said quantitative detection;

(H) providing an indicator capable of converting said signal into an indication of said concentration of said alcohol in said liquid; and (I) intermittently and cyclically purging said measuring chamber with a controlled stream of a purge gas fed into said inlet port of said measuring chamber.

19. A probe for in-line measurement of a concentration of a normally volatile alcohol in a flowing liquid comprising:

(A) a membrane that is permeable to vapors of said alcohol but substantially impermeable to said liquid, said membrane mounted in a flow chamber;

(B) a measuring chamber having an open end closed against said liquid by said membrane and have an inlet and an outlet;

(C) a pressure means for feeding a purge gas via said inlet into said measure chamber and out of said chamber by means of said outlet, and at least one valve for intermittently and cyclically controlling passage of said purge gas through said measuring chamber; and (D) a detector arranged within said measuring chamber capable of an essentially quantitative detection of said alcohol and of generating an electrical signal in proportion with said detection.

20. A method of in-line measurement of a normally volatile alcohol in a flowing liquid comprising:

(E) contacting said flowing liquid with a membrane that is permeable to vapors of said alcohol but substantially impermeable to said liquid, said membrane mounted in a floor chamber;

(F) providing a measuring chamber having an open end closed against said liquid by said membrane and having an inlet port and an outlet port;

(G) providing a detector within said measuring chamber capable of an essentially quantitative detection of said alcohol and of generating an electrical signal in relation with said quantitative detection;

(H) providing an indicator capable of converting said signal into an indication of said concentration of said alcohol in said liquid; and (I) intermittently and cyclically purging said measuring chamber with a controlled stream of a purge gas fed into said inlet port of said measuring chamber.

* * * * *